United States Patent [19]

Hoefer

[11] 3,980,540
[45] Sept. 14, 1976

[54] VERTICAL GEL SLAB ELECTROPHORESIS APPARATUS AND METHOD

[75] Inventor: Stanton A. Hoefer, San Francisco, Calif.

[73] Assignee: Hoefer Scientific Instruments, San Francisco, Calif.

[22] Filed: Aug. 18, 1975

[21] Appl. No.: 605,242

Related U.S. Application Data

[62] Division of Ser. No. 455,871, March 28, 1975, Pat. No. 3,932,265.

[52] U.S. Cl. .......................... 204/180 G; 204/299 R
[51] Int. Cl.² .......................................... G01N 27/26
[58] Field of Search ............ 204/180 R, 180 G, 299

[56] References Cited
UNITED STATES PATENTS

| | | | |
|---|---|---|---|
| 3,129,158 | 4/1964 | Raymond et al. | 204/180 G |
| 3,799,863 | 3/1974 | Zeineh | 204/299 |
| 3,879,280 | 4/1975 | Peterson et al. | 204/299 |

*Primary Examiner*—John H. Mack
*Assistant Examiner*—A. C. Prescott
*Attorney, Agent, or Firm*—Flehr, Hohbach, Test, Albritton & Herbert

[57] ABSTRACT

A gel electrophoresis device in which the separating gel is cast in a vertical position between hydrophilic plates which form a gel slab chamber filled with a separating gel solution from the bottom for reducing fill turbulence allowing formation of a gel slab having a predetermined gradient. A removable seal is applied to the bottom of the gel slab chamber for containing the separating gel solution prior to polymerization. One gel slab chamber may be removably attached to each vertical side of a central temperature control chamber which is completely enclosed and which has an inlet and an outlet channel for circulation of temperature control fluid therethrough. An upper buffer chamber which opens upwardly is formed above the central temperature control chamber in communication with the top of the vertical gel slab chambers. The top of the gel slab is formed using a well forming implement made of polymerization inhibiting material so that the implement may be withdrawn after polymerization without altering the desired shape of the top of the vertical gel slab. The gel slab chambers attached to the central enclosed temperature control and upper buffer chamber are lowered into an outer chamber after polymerization of the separating gel solution and removal of the seals from the lower end of the gel slab chambers. The outer container is filled with a buffer solution in consequent directi contact with the lower end of the gel slabs, and the upper buffer chamber is filled with a buffer solution in direct contact with the top of the gel slabs. Samples are underlaid beneath the upper buffer solution atop the shaped upper surface of the gel slabs and a cover is placed on the outer container to contact a pair of electrodes which are in separate electrical contact with one of the upper and lower buffer chambers for applying a voltage therebetween, thereby causing electrophoretic separation of the sample within the gel slab.

4 Claims, 7 Drawing Figures

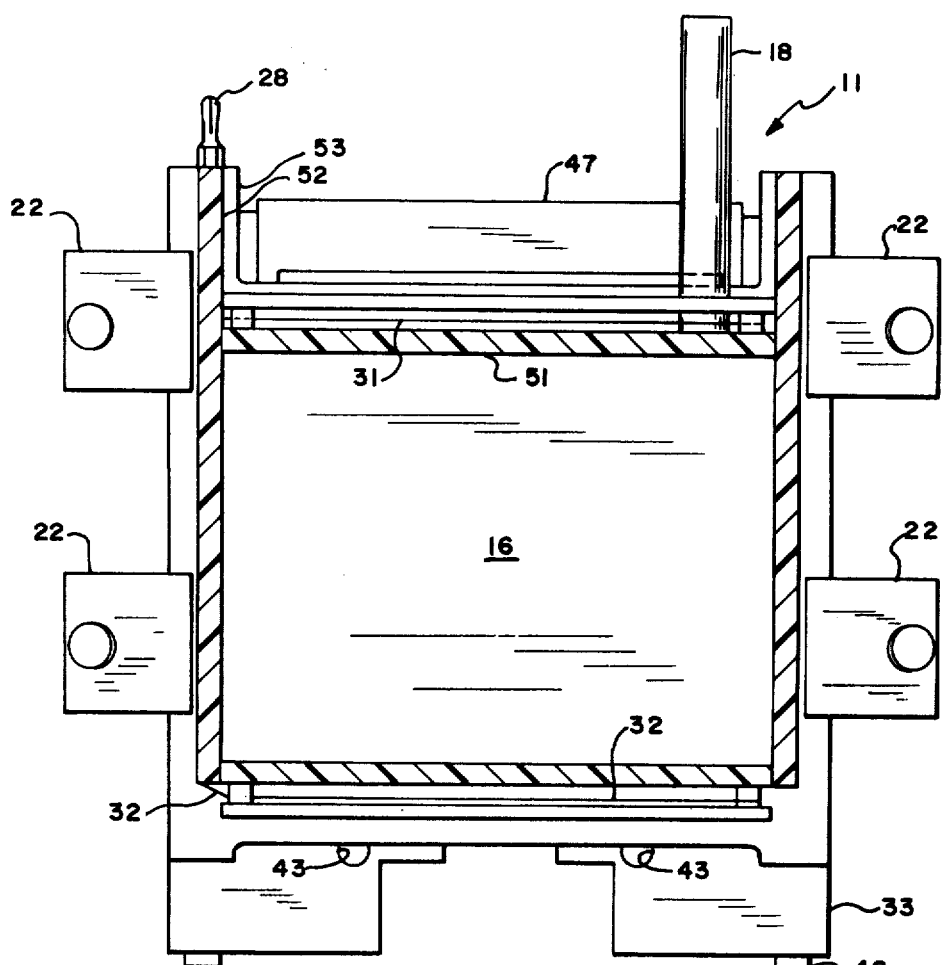
FIG.—3
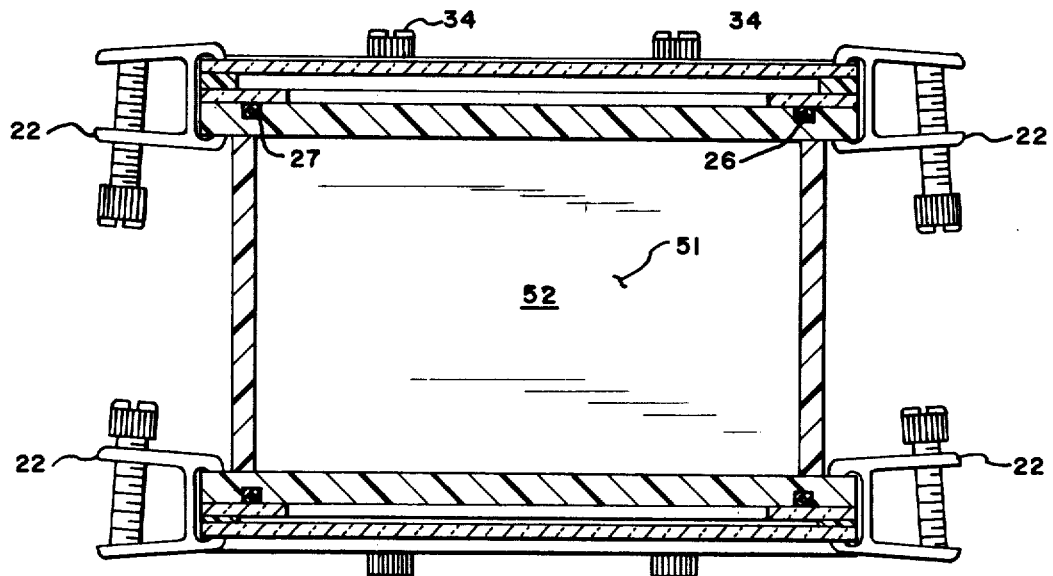
FIG.—4

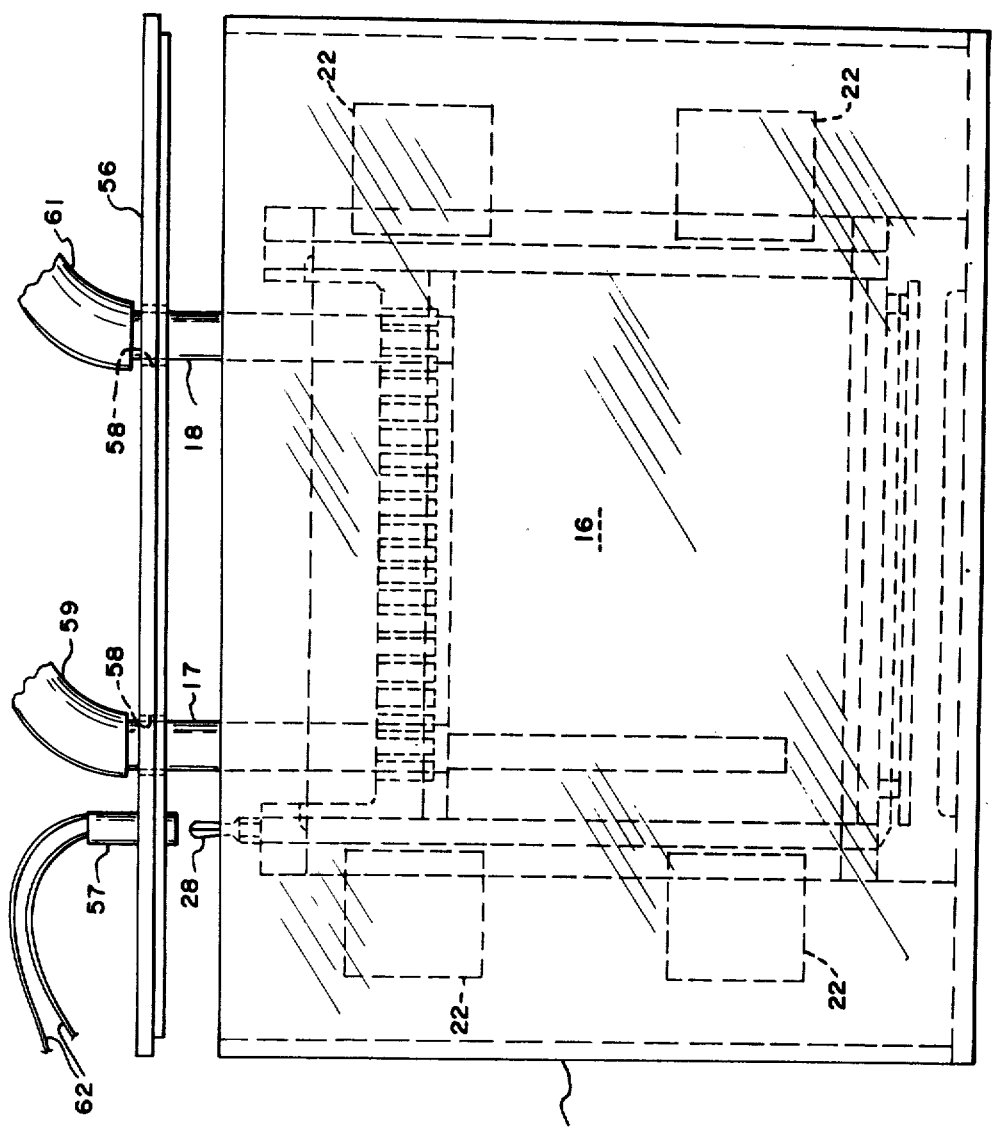
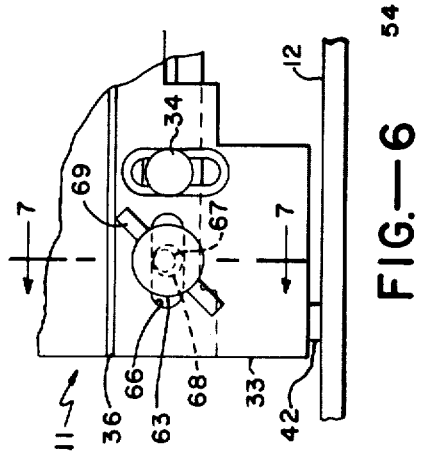
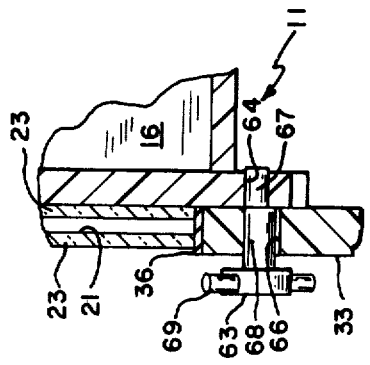
FIG.—5
FIG.—6
FIG.—7

VERTICAL GEL SLAB ELECTROPHORESIS APPARATUS AND METHOD

This is a division of application Ser. No. 455,871 filed Mar. 28, 1975 now U.S. Pat. No. 3,932,265.

BACKGROUND OF THE INVENTION

1. Field of the Invention

This invention relates to a vertical gel slab formation and electrophoresis apparatus, and more particularly to an apparatus in which gel slabs are formed in a gel slab chamber oriented in a true vertical position, having hydrophilic side walls, and which is filled from the bottom for eliminating turbulence and preserving separating gel solution gradients.

2. Description of the prior art

Most prior slab electrophoresis devices do not provide for vertical casting of the gel slab thereby trapping bubbles within the gel slab which distorts the separation of the sample therein during electrophoresis. Those devices providing for vertical casting of the gel slab do not have means for orienting the gel slab chamber in a true vertical position prior to polymerization and are all filled with the separating gel solution from the top of the gel slab chamber thereby increasing the probability of bubble formation and turbulence during filling which destroys or distorts any desired separating gel gradient. Gel slabs often allow leakage of buffer solution between the gel slab and the sides of the gel slab chamber, thereby short circuiting the gel slab and distorting the desired separation of the sample within the slab during electrophoresis. Moreover, low concentration separating gel solutions were often distorted due to a disparity of vertical forces at the bottom of the gel slab arising from different fluid pressure heads in the gel slab chamber and the lower buffer chamber. Operator exposure to high voltages utilized during electrophoresis is possible in prior art devices.

A vertical gel slab formation and electrophoresis apparatus is therefore needed which will allow casting of gel slabs having predetermined gel gradients, eliminate deformation within low concentration gel slabs, prevent leakage of buffer solution through the gel slab chamber, and provide operator protection from electrical shock.

SUMMARY OF THE INVENTION AND OBJECTS

An apparatus is disclosed which allows vertical formation of a gel slab for use in electrophoresis within a gel slab chamber having separable vertical hydrophilic side walls and separable vertical end walls which promote a bond with a polymerized gel solution. A removable seal is placed across the bottom end of the gel slab chamber supported by removable means adapted to admit filling device for filling the gel slab chamber from the bottom. The vertical end walls enhancing polymerization serve to firmly hold the gel slab within the chamber after polymerization when the bottom seal is removed. Ajustable means secure all of the vertical walls of the gel slab chamber together in a unitary assembly. The gel slab chamber is placed in an outer container so that the lower end of the gel slab chamber is in communication with a buffer solution placed in the outer container. An upper buffer chamber is also placed in the outer container in communication with the top of the vertical gel slab. The upper buffer chamber is filled with a buffer solution, and a separate electrode is placed in electrical contact with the buffer solution in each of the upper and lower buffer chambers. A sample is underlaid beneath the upper buffer solution on top of the vertical gel slab and an electrical potential is applied between the electrodes for causing the separation of the sample within the gel slab electrophoretically.

In general it is an object of the present invention to provide a vertical gel slab electrophoresis apparatus in which the gel slab is cast in a truly vertical position for eliminating discontinuities in the gel slab due to trapped bubbles.

It is another object of the present invention to provide a vertical gel slab electrophoresis apparatus which prevents buffer solution leakage and which holds a gel slab firmly within the chamber after polymerization.

It is another object of the present invention to provide a vertical gel slab electrophoresis device in which the gel slab chamber may be filled from the bottom for preserving the gradient in a separating gel solution.

It is another object of the present invention to provide a vertical gel slab electrophoresis apparatus in which a plurality of samples may be separated simultaneously under identical conditions.

It is another object of the present invention to provide a vertical gel slab electrophoresis apparatus in which the operator is protected from electrical shock.

It is another object of the present invention to provide a vertical gel slab electrophoresis apparatus in which hydrostatic equilibrium is maintained across the bottom surface of the gel slab to prevent distortion therein.

It is another object of the present invention to provide a vertical gel slab electrophoresis apparatus in which the gel slab chamber is separable for easy removal of the gel slab after electrophoresis.

It is another object of the present invention to provide a vertical gel slab electrophoresis apparatus in which the gel slab chamber is filled, the gel slab is polymerized, and the sample is separated within the gel slab without disturbing the gel slab chamber.

It is another object of the present invention to provide a vertical gel slab electrophoresis apparatus which may be used as a preparative electrophoresis device.

Additional objects and features of the invention will appear from the following description in which the preferred embodiment has been set forth in detail in conjunction with the accompanying drawings.

BRIEF DESCRIPTION OF THE DRAWINGS

FIG. 3 is a sectional view along the line 3—3 of FIG. 2.

FIG. 4 is a sectional view along the line 4—4 of FIG. 1.

FIG. 5 is a side elevational view of the inner container within an outer container and a cover poised above the top of the outer container.

FIG. 6 is a partial side elevational view showing a gel slab chamber sealing cam configuration.

FIG. 7 is a sectional view along the line 7—7 of FIG. 6.

DESCRIPTION OF THE PREFERRED EMBODIMENT

Figure 1:
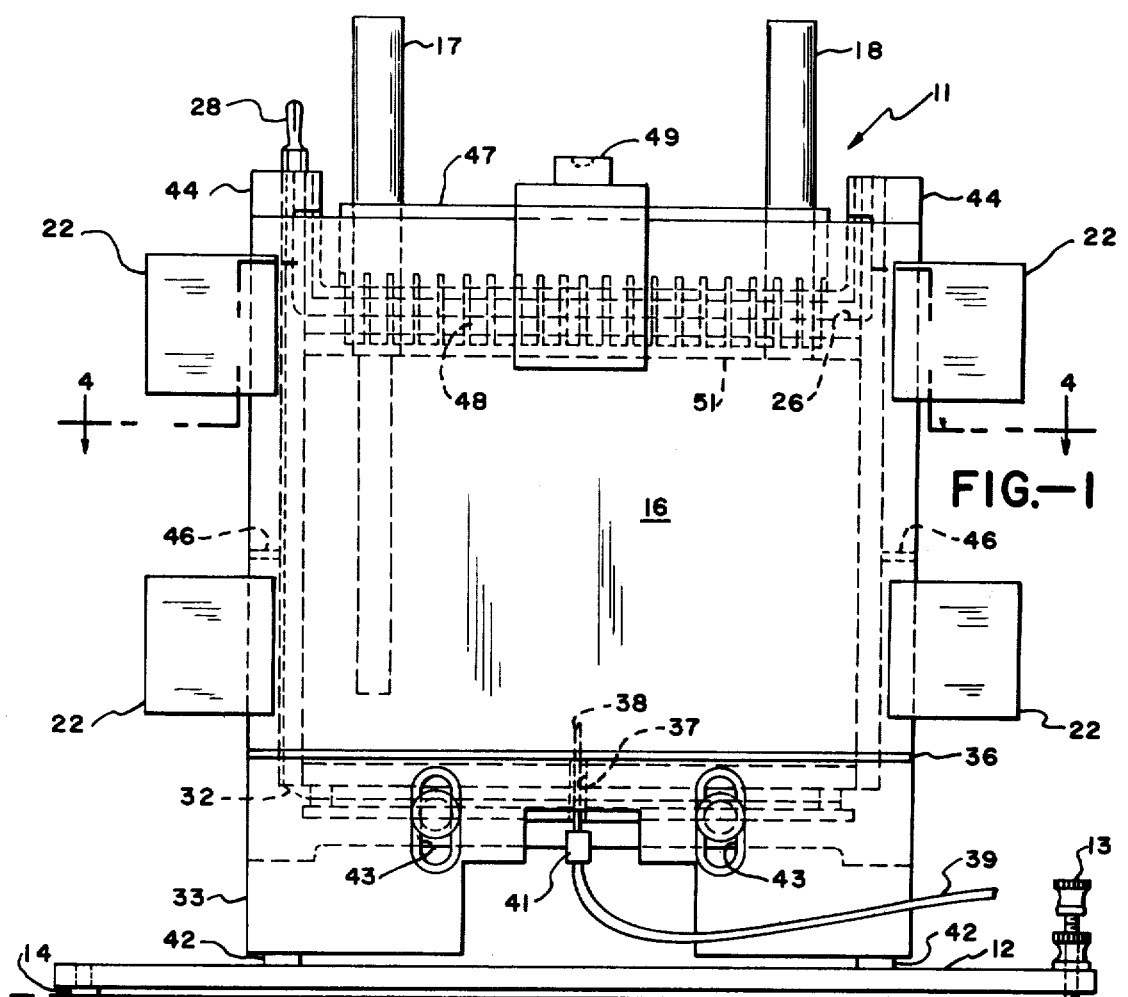
FIG. 1 is a side elevational view of the inner container and the gel slab chambers on a leveling plate.

The vertical gel slab formation and electrophoresis apparatus disclosed herein provides advantages heretofore unavailable in gel slab electrophoresis devices. Referring to FIG. 1 an inner container 11 is shown mounted atop leveling plate 12 supported at three points. Two points are adjustable in height by screws 13 and the third point is provided by nonadjustable foot 14. An enclosed chamber 16 has an inlet 17 and an outlet 18 for circulating a temperature control fluid therethrough.

Figure 2:
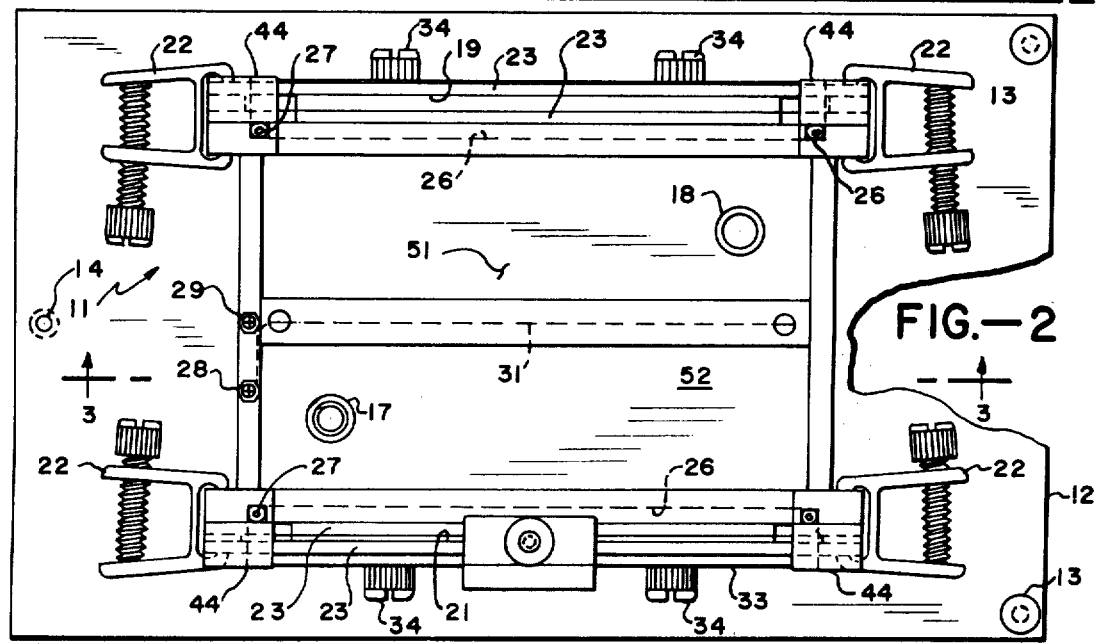
FIG. 2 is a plan view of the inner container and the gel slab chambers on the leveling plate.

Referring to FIG. 2 a vertical gel slab chamber 29 of one thickness and a vertical gel slab chamber 21 of a lesser thickness is shown mounted on either side of inner container 11 by adjustable clamps 22. Both gel slab chambers 19 and 21 have separable opposing vertical side walls 23 of a hydrophilic material such as glass. Gel slab chambers 19 and 21 also have separable opposing vertical end walls or spacers 24 made of a material which promotes a bond with a polymerized gel solution. A groove 26 having a general U-shape opening upwardly has inserted therein a seal 27 for contacting vertical side wall 23 nearest the vertical side of inner container 11. It may be seen in FIG. 2 that adjustable clamps 22 secure side walls 23 and end walls 24 together in a unitary assembly, and also secure the unitary assembly to the vertical sides of inner container 11.

Electrodes 28 and 29 are mounted atop the end walls of inner container 11 and have electrical conductors 31 and 32 extending therefrom respectively.

Supporting members 33 are attached to the lower portion of inner container 11 by means of screws 34. A sealing gasket 36 is attached to the top of supporting members 33 for sealing the bottom of each of gel slab chambers 19 and 21. A passage 37 is formed in a vertical direction centrally located along supporting members 33 for providing access to sealing gasket 36 for penetration thereof by hypodermic needle 38. Sealing gasket is self sealing to maintain the bottom seal in gel slab chambers 19 and 21 when hypodermic needle 38 is removed. Tubing 39 is connected to hypodermic needle 38 by tapered connecter 41 for bottom filling of gel slab chambers 19 and 21 with a separating gel solution. Supporting members 33 rest on leveling plate 12 by means of resilient feet 42 attached to the bottom thereof. Supporting members 33 also have elongate holes 43 for allowing passage of screws 34 so that gasket 36 may be firmly pressed upward against the bottom of gel slab chambers 19 and 21 as hereinafter described prior to tightening screws 34 to provide a positive seal for the bottoms of chambers 19 and 21. Blocks 44 are attached to the upper portion of inner container 11 to serve as stops for the upper edge of the walls 23 and 24 forming gel slab chambers 19 and 21. Separable opposing vertical end walls 24 may have apertures 46 passing therethrough, in one embodiment, which are in communication with gel slab chambers 19 and 21.

A comb 47 is provided for insertion into the top of gel slab chambers 19 and 21 having teeth 48 formed thereon for casting sample wells in the tops of the gel slabs which are formed therein. A leveling device such as a bubble level indicator 49 is provided which is placed atop comb 47 or vertical side walls 23, depending upon the phase of the process.

A top wall 51 located with inner container 11, together with the end walls, side walls and the bottom wall of inner container 11, defines enclosed chamber 16. The space above top wall 51 within extensions of the end walls of inner container 11 and then outer vertical side walls of gel slab chambers 19 and 21 defines an upwardly opening upper buffer chamber 52.

Referring to FIG. 3 the inner vertical side wall 23 of both gel slab chambers 19 and 21 has a notch 53 placing the upper end of gel slab chambers 19 and 21 in communication with upper buffer chamber 52. Conductor 31 is supported internally extending through upper buffer chamber 52.

FIG. 4 clearly shows the manner in which the side walls 23 and the end walls 24 are secured together in a unitary assembly to the sides of inner container 11. The seal 27 in groove 26 is shown for providing a seal at the inner vertical side wall 23 for upper buffer chamber 52. Sections of the upper adjustable clamps 22 and comb 47 are omitted in FIG. 4 for clarity.

FIG. 5 shows inner container 11 positioned inside of an outer container 54 having a cover 56. Cover 56 includes a pair of female connectors 57 for mating with electrodes 28 and 29. Cover 56 also has holes 58 located therein for passing inlet 17 and outlet 18 from enclosed chamber 16. Tubes 59 and 61 are provided to mate with inlet 17 and outlet 18 respectively for carrying temperature controlling fluid to and from enclosed chamber 16. Electrical conductors 62 are shown for providing an electrical potential between female connectors 57 in cover 56.

The manner in which the vertical slab electrophoresis apparatus is used for microanalytical biochemical analysis will now be described. As stated above, the unit accomodates two gel slabs, each of which may have as many as twenty sample wells. Each slab is in contact with the same upper and lower buffer chambers providing for uniformity of buffer conditions and consequent equal current distribution through the gel slabs. One of the leakproof characteristics of the unit is provided by vertical side walls 23 which are hydrophilic. Glass is a hydrophilic substance and has been used for side walls 23 since it forms a strong bond with the gel, minimizing band widening and streaking, and also minimizing leakage of the buffer solution between the gel slab and the side walls 23. Seal 27 in groove 26 may be a silicone rubber gasket providing a positive seal between the glass plates 23 and the sides of inner container 11. From the above it may be seen that electrically conductive paths between the buffer solution in the upper buffer chamber 52 and the buffer solution contained in the outer container 54 due to buffer solution leakage are eliminated.

The electrophoresis unit is assembled in the following manner. Inner container 11 is placed on its side and vertical side wall 23 having notch 53 in communication with upper chamber 52 is placed adjacent to a side wall of inner container 11 in contact with seal 27. A gel slab thickness is determined and appropriate thickness polyvinylchloride vertical end walls 24 are placed along the edges of the notched vertical side wall 23. The other vertical side wall 23 is placed over the vertical end walls 24 to form the four vertical walls of the gel slab chamber 19 or 21. The notch 53 in the inner vertical side wall 23 is aligned with a matching notch in the upper buffer chamber 52. Vertical side and end walls 23 and 24 are then clamped securely together and to inner container 11 by means of adjustable clamps 22 as shown in the figures.

After securing the unitary assemblies forming gel slab chambers 19 and 21 to opposite sides of inner container 11, supporting members 33 carrying gaskets 36 are placed on the lower portions of inner container 11 and screws 34 are inserted through elongate holes 43 to engage threaded holes in the lower portions of inner container 11. Gaskets 36 are pressed securely against the bottoms of gel slab chambers 19 and 21 and screws 34 are securely tightened, thereby sealing the bottoms of gel slab chambers 19 and 21. Separate means, such as a rotatable cam 63 shown in FIGS. 6 and 7, in conjunction with a pair of holes 64 in the lower extensions of the side walls on inner container 11, and a matching pattern of elongate holes 66 in supporting members 33, may be sued to gain the contact pressure between gaskets 36 and the bottoms of chambers 19 and 21. Cam 63 has a centered extension 67 with a diameter fitting hole 64 projecting from an eccentric cam portion 68 attached to a turning handle 69 for rotatable cam 63. Cam portion 68 will pass through elongate hole 66. To move members 33 toward the bottom of chambers 19 and 21 to press gasket 36 firmly therebetween, extension 67 is inserted through elongate hole 66 and fit into hole 64. Cam portion 68 is situated in elongage hole 66 and clockwise or counterclockwise turning of handle 69 will force the surface of cam portion 68 into contact with the wall of hole 66, moving support member 33 toward the bottom of chambers 19 and 21.

Hypodermic needle 38 is inserted through passages 37 in supporting members 33 to penetrate sealing gaskets 36 and project into gel slab chambers 19 and 21. A separating gel solution is introduced into gel slab chambers 19 and 21 through the bottom thereof until the separating gel solution approaches a level below the end of the sample well forming comb 47. Leveling device 49 is placed on the top of vertical side walls 23 and the gel slab chambers 19 and 21 are adjusted to assume a true vertical position by adjusting leveling plate 12 by means of leveling screws 13. In this fashion gel slabs formed in chambers 19 and 21 are produced which have a substantially constant height across the entire width of the slab. For pumping acrylamide gradients into gel slab chambers 19 and 21, a flow rate of 0.5 to 1.0 milliliters per minute is recommended. Hypodermic needle 38 is removed and seal 36 self seals the point of penetration. An even aqueous overlayer is placed atop the lower separating gel solution to provide a smooth separating surface and the gel solution is polymerized. After polymerization, the overlay fluid is drained from the top of the separating gel and the top surface rinsed. All fluid is then removed from the top surface of the separating gel. The comb 47 having a desired number of teeth 48 for forming sample wells is then intorduced into the top of the gel slab chambers 19 and 21— leveling device 49 is placed atop comb 47 and a stacking gel is placed in the top of the gel slab chambers. A level condition should still exist, but adjustment may be made as before.

An aqueous solution is overlaid above the stacking gel and the stacking gel is polymerized. After polymerization of the stacking gel, comb 47 is removed and the top of the stacking gel is rinsed. At this point the sealing gasket 36 held in place by supporting members 33 are removed by removing screws 34. Inner container 11 is then placed inside outer container 54. Outer container 54 is filled with buffer solution and now constitutes a lower buffer chamber. Upper buffer chamber 52 is also filled with buffer solution to the same level as outer container 54, and samples are underlaid beneath the upper buffer solution into the sample wells formed by teeth 48 in combs 47. The lid 56 is placed upon outer container 54 thereby encompassing electrodes 28 and 29 with female connectors 57. Electrical conductor 32 extends into the lower buffer chamber. An electrical potential is applied between conductors 62 and consequently between electrodes 28 and 29 for separating the samples in the sample wells electrophoretically.

After electrophoresis cover 56 is removed, inner container 11 is lifted out of outer container 54, adjustable clamps 22 are loosened and gel slab chambers 19 and 21 are separated from inner container 11. Vertical side walls 23 are pried apart and the gel slab is removed from the vertical side wall 23 upon which it rests by directing a stream of water between the gel slab and the glass side wall 23.

The thickness of the gel slab is determined by the size of the separable opposing vertical end walls 24. Comb 47 is selected to have a thickness substantially the same as the thickness of vertical end walls 24. In this fashion the operator is provided with a choice of gel thickness.

The standard comb 47 has 20 sample well forming teeth 48 which are 4 millimeters wide and 15 millimeters long. The space between each tooth is 2.5 millimeters in one embodiment. The teeth are designed to permit the escape of air bubbles that would otherwise deform the shape of the sample well. As stated above the comb 47 is made of a material which inhibits polymerization to facilitate the removal of the comb after polymerization without tearing the surrounding gel.

During both the polymerization and electrophoresis phases of the process, a coolant is circulated through the enclosed chamber 16 which dissipates heat evenly from the inner wall 23 of both gel slab chambers 19 and 21. Heat is also evenly dissipated from the upper and lower buffer chambers by means of the coolant circulating through enclosed chamber 16.

It may be noted by reference to FIG. 5 that outer container 54 may be filled to the same level as inner buffer chamber 52. In this fashion hydrostatic equilibrium at the bottom surface of the gel slabs in chambers 19 and 21 is achieved which prevents distortion in low concentration gels. It should also be noted that cover 56 carries the electrical potential in female connectors 57 which is only connected to electrodes 28 and 29 when cover 56 is placed atop outer container 54. This feature prevents injury from electrical shock to an operator through inadvertent contact with the inner or the outer buffer solution with the cover removed and a high voltage applied.

The vertical gel slab electrophoresis apparatus disclosed herein has an additional utility as a preparative electrophoresis device when apertures 46 are formed in opposing vertical end walls 24. When the apparatus is used in this mode, gel slab chambers 19 and 21 are filled to a point just below apertures 46 with a high concentration acrylamide gel solution, for example, which forms a dense gel plug upon polymerization. Thereafter, a non-polymerizing fluid is laid atop the lower polymerized gel to a thickness of approximately 1 millimeter. An upper separating gel solution is carefully laid atop the non-polymerizing fluid to a point just below teeth 48 on comb 47 as described above. The upper separating gel solution is polymerized and the remainder of the process proceeds as described above.

During electrophoresis when the apparatus is being used as a preparative electrophoresis device, buffer solution 1s continually circulated through one aperture 46 and out of the other aperture 46 by means of conduits (not shown) in communication therewith. The buffer solution is transmitted to a collecting device for collecting predetermined portions of the sample after it has migrated through the upper portion of the seperating gel. Apertures 46 are not present in vertical end walls 24 unless the apparatus is being used as a preparative electrophoresis device.

A vertical gel slab electrophoresis apparatus and method has been disclosed which prevents leakage between the hydrophilic vertical side walls of the gel slab chambers and the gel slab and which provides for a plurality of samples to be electrophoresed through two separate gel slabs simultaneously under identical electrical potential and temperature conditions. An apparatus and method is disclosed providing for bottom filling of the gel slab chambers with separating gel solution whereby filling turbulence will not disturb desired separating gel gradient characteristics. Vertical end walls of the gel slab chambers are provided which promote a bond with a polymerized gel solution for retaining the gel slabs within the gel slab chambers after electrophoresis.

Sample well forming implements are provided which inhibit polymerization for easy removal of the implements after the sample wells are formed through polymerization. Operator protection and hydrostatic equilibrium at the bottom surface of the gel slabs is provided in the apparatus. A single assembly is provided for filling, polymerizing and electrophoresis all within the same unit. Accurate temperature control for casting of gel slabs and electrophoresis is provided.

I claim:

1. A method of preparing a vertical gel slab for use in electrophoresis without disturbing the gel slab until electrophoresis is completed comprising the steps of forming a gel slab chamber having hydrophilic walls, orienting the gel slab chamber in a vertical direction, sealing the bottom of the gel slab chamber filling the gel slab chamber from the bottom with a separating gel solution while the gel slab chamber is in a vertical position, polymerizing the separating gel solution, removing the seal from the lower end of the gel slab chamber, placing the gel slab chamber in a container with the bottom of the gel slab in contact with a buffer solution, placing the upper end of the gel slab in contact with a separate buffer solution, underlaying a sample beneath the separate buffer solution above the gel slab, applying an electrical potential between the buffer solution and the separate buffer solution, whereby the sample is separated electrophoretically in the gel slab.

2. A method for producing a vertical gel slab and separating a sample therein electrophoretically as in claim 1 together with the steps of providing an even aqueous overlayer on the separating gel prior ot polymerization, draining the aqueous overlayer after polymerization, inserting a sample well forming comb above the polymerized gel slab, overlaying the polymerized gel slab with a stacking gel to a level above the lower level of the well forming comb, polymerizing the stacking gel, removing the sample well forming comb, and wherein the step of underlaying a sample beneath the separate buffer solution includes placing a sample in each of a plurality of the sample wells formed by the comb, whereby a plurality of samples may be separated electrophoretically under identical conditions.

3. A method of forming a gel slab vertically and separating a sample therein elecrophoretically as in claim 1 together with the step of leveling the gel slab chamber prior to polymerizing the separating gel solution so that the gel slab formed therein has a substantially constant height along the width of the slab.

4. A method of forming a gel slab vertically and separating a sample therein electrophoretically as in claim 1 wherein the step of filling the gel slab chamber from the bottom with a separating gel solution includes the step of stopping the fill at an intermediate level in the gel slab chamber, and wherein the step of polymerizing the separating gel is followed by the steps of laying a shallow layer of non-polymerizing fluid atop the lower polymerized separating gel, laying an upper layer os separating gel solution atop the non-polymerizing fluid, polymerizing the upper layer of separating gel, and flushing the space occupied by the non-polymerizing fluid with a buffer solution during electrophoresis for carrying away and collection of desired sample components after migration through the upper layer of the separating gel, whereby a preparative electrophoresis process is performed.

* * * * *